United States Patent [19]

Alaimo

[11] 4,012,409
[45] Mar. 15, 1977

[54] N-(6-ETHYL-4-THIOCYANATO-2-BENZO-THIAZOLYL)-5-NITROFURAMIDE

[75] Inventor: Robert J. Alaimo, Norwich, N.Y.
[73] Assignee: Morton-Norwich Products, Inc., Norwich, N.Y.
[22] Filed: Dec. 29, 1975
[21] Appl. No.: 644,620
[52] U.S. Cl. .............................. 260/305; 424/270
[51] Int. Cl.$^2$ .................................. C07D 419/00
[58] Field of Search .................. 260/305; 424/285
[56] References Cited
UNITED STATES PATENTS 3,706,759   12/1972   Alaimo et al. ............... 260/305

OTHER PUBLICATIONS

Wagner et al., Synthetic Organic Chemistry, Wiley, NYC, 1953, Section 348.

*Primary Examiner*—Richard J. Gallagher
*Attorney, Agent, or Firm*—Anthony J. Franze

[57] ABSTRACT

N-(6-ethyl-4-thiocyanato-2-benzothiazolyl)-5-nitrofuramide is an effective agent against coccidiosis in the chicken.

1 Claim, No Drawings

N-(6-ETHYL-4-THIOCYANATO-2-BENZOTHIAZOLYL)-5-NITROFURAMIDE

This invention relates to the chemical compound N-(6-ethyl-4-thiocyanato-2-benzothiazolyl)-5-nitrofuramide and a method for preparing it.

The compound of this invention possesses anti-coccidial action. When administered in feed at 0.022% by weight thereof the title compound provided 100% mortality protection against *Eimeria tenella* in chickens.

The method of making the compound of this invention consists in bringing together 2-amino-6-ethyl-4-thiocyanatobenzothiazole and 5-nitro-2-furoyl chloride in the presence of a solvent such as pyridine under the influence of heat. It is illustrated by this example:

N-(6-ethyl-4-thiocyanato-2-benzothiazolyl)-5-Nitrofuramide

To a solution of 2-amino-6-ethyl-4-thiocyanatobenzothiazole (6 g, 0.025 mole) in pyridine (50 ml) was added 5-nitro-2-furoyl chloride (4.5 g, 0.025 mole). The stirred mixture was heated for 30 minutes, then chilled in an ice bath and filtered. After thorough washing with ethanol the air dried product weighed 8.5 g (91%). Recrystallization from ethanol/dimethylformamide provided an analytical sample which melted at 229°–231°.

Analysis — Calcd. for $C_{15}H_{10}N_4O_4S_2$ (Percent): C, 48.12, H, 2.69; N, 14.97 Found (Percent): C, 47.93; H, 2.93; N, 14.91.

What is claimed is:
1. N-(6-ethyl-4-thiocyanato-2-benzothiazolyl)-5-nitrofuramide.

* * * * *